United States Patent
McKenzie et al.

(10) Patent No.: US 8,882,511 B2
(45) Date of Patent: Nov. 11, 2014

(54) SYSTEM, METHOD AND MEDIUM FOR SIMULATING NORMAL AND ABNORMAL MEDICAL CONDITIONS

(75) Inventors: Frederic D. McKenzie, Norfolk, VA (US); Hector M. Garcia, Norfolk, VA (US); Reynel J. Castelino, Norfolk, VA (US); Thomas W. Hubbard, Norfolk, VA (US); John A. Ullian, Norfolk, VA (US); Gayle A. Gliva-McConvey, Virginia Beach, VA (US); Robert J. Alpino, Williamsburg, VA (US)

(73) Assignee: Eastern Virginia Medical School, Norfolk, VA (US)

( * ) Notice: Subject to any disclaimer, the term of this patent is extended or adjusted under 35 U.S.C. 154(b) by 1881 days.

(21) Appl. No.: 11/666,244

(22) PCT Filed: Oct. 25, 2005

(86) PCT No.: PCT/US2005/038150
§ 371 (c)(1),
(2), (4) Date: Aug. 20, 2009

(87) PCT Pub. No.: WO2006/047400
PCT Pub. Date: May 4, 2006

(65) Prior Publication Data
US 2009/0305212 A1    Dec. 10, 2009

Related U.S. Application Data

(60) Provisional application No. 60/621,084, filed on Oct. 25, 2004.

(51) Int. Cl.
*G09B 23/28* (2006.01)
*G06F 19/00* (2011.01)

(52) U.S. Cl.
CPC ............ *G06F 19/3437* (2013.01); *G09B 23/28* (2013.01)
USPC ............................ 434/262; 434/267; 434/268

(58) Field of Classification Search
USPC .......................................... 434/262, 267, 268
See application file for complete search history.

(56) References Cited

U.S. PATENT DOCUMENTS 2,945,304 A * 7/1960 Niiranen et al. ............... 434/268
3,024,568 A * 3/1962 Barnett ......................... 446/397

(Continued)

FOREIGN PATENT DOCUMENTS

| JP | 01-196091 | 8/1989 |
| JP | 2004-520606 A1 | 7/2004 |
| WO | WO 2005114616 A1 * | 12/2005 | ............. G09B 19/00 |

OTHER PUBLICATIONS

English Translation of Office Action dated Jul. 20, 2011 for corresponding Japanese Patent Application No. 2007-539020.

(Continued)

*Primary Examiner* — Nikolai A Gishnock
(74) *Attorney, Agent, or Firm* — Wilmer Cutler Pickering Hale and Dorr LLP

(57) ABSTRACT

The present invention provides a system, method and medium for simulating medical conditions to facilitate medical training, that utilizes a roaming device configured to be mobile; a positioning device configured to determine location information of the roaming device; and a computing device configured to receive the location information, compare the location information with a predetermined set of regions, and transmit information indicative of a medical condition when the location information coincides with the predetermined set of regions.

15 Claims, 7 Drawing Sheets

(56) References Cited

U.S. PATENT DOCUMENTS

| | | | |
|---|---|---|---|
| 3,947,974 A * | 4/1976 | Gordon et al. | 434/266 |
| 4,155,196 A * | 5/1979 | Bollinger et al. | 446/130 |
| 4,337,529 A * | 6/1982 | Morokawa | 377/20 |
| 4,411,629 A * | 10/1983 | Voights | 434/266 |
| 5,047,952 A * | 9/1991 | Kramer et al. | 704/271 |
| 5,119,072 A * | 6/1992 | Hemingway | 340/573.1 |
| 5,217,453 A * | 6/1993 | Wilk | 606/7 |
| 5,256,098 A * | 10/1993 | Smith et al. | 446/28 |
| 5,360,005 A * | 11/1994 | Wilk | 600/437 |
| 5,491,756 A * | 2/1996 | Francais | 381/332 |
| 6,097,822 A * | 8/2000 | Min | 381/301 |
| 6,106,463 A * | 8/2000 | Wilk | 600/437 |
| 6,149,595 A * | 11/2000 | Seitz et al. | 600/438 |
| 6,220,866 B1 | 4/2001 | Amend et al. | |
| 6,319,201 B1 * | 11/2001 | Wilk | 600/437 |
| 6,443,735 B1 * | 9/2002 | Eggert et al. | 434/262 |
| 6,503,087 B1 * | 1/2003 | Eggert et al. | 434/262 |
| 6,527,558 B1 * | 3/2003 | Eggert et al. | 434/262 |
| 6,758,676 B2 * | 7/2004 | Eggert et al. | 434/262 |
| 7,114,954 B2 * | 10/2006 | Eggert et al. | 434/262 |
| 7,122,005 B2 * | 10/2006 | Shusterman | 600/300 |
| 7,192,284 B2 * | 3/2007 | Eggert et al. | 434/268 |
| 7,497,828 B1 * | 3/2009 | Wilk et al. | 600/443 |
| 7,510,398 B1 * | 3/2009 | Thornton | 434/262 |
| 7,597,665 B2 * | 10/2009 | Wilk et al. | 600/459 |
| 7,645,141 B2 * | 1/2010 | Lecat | 434/266 |
| 7,976,312 B2 * | 7/2011 | Eggert et al. | 434/267 |
| 7,976,313 B2 * | 7/2011 | Eggert et al. | 434/268 |
| 8,016,598 B2 * | 9/2011 | Eggert et al. | 434/268 |
| 8,152,532 B2 * | 4/2012 | Eggert et al. | 434/267 |
| 8,257,089 B2 * | 9/2012 | Lecat | 434/266 |
| 8,287,283 B2 * | 10/2012 | Lecat | 434/266 |
| 8,323,031 B2 * | 12/2012 | Lecat | 434/268 |
| 8,419,438 B2 * | 4/2013 | Eggert et al. | 434/268 |
| 8,696,362 B2 * | 4/2014 | Eggert et al. | 434/266 |
| 2001/0001852 A1 * | 5/2001 | Rovinelli et al. | 703/22 |
| 2002/0087101 A1 | 7/2002 | Barrick et al. | |
| 2002/0100103 A1 * | 8/2002 | Pascal | 2/102 |
| 2003/0073060 A1 * | 4/2003 | Eggert et al. | 434/262 |
| 2003/0091968 A1 * | 5/2003 | Eggert et al. | 434/262 |
| 2003/0139671 A1 | 7/2003 | Walston et al. | |
| 2003/0210186 A1 | 11/2003 | Sollenberger et al. | |
| 2004/0022052 A1 * | 2/2004 | Chien | 362/84 |
| 2004/0157199 A1 * | 8/2004 | Eggert et al. | 434/262 |
| 2004/0157612 A1 | 8/2004 | Kim | |
| 2004/0161732 A1 * | 8/2004 | Stump et al. | 434/262 |
| 2004/0197764 A1 | 10/2004 | Stump et al. | |
| 2004/0228494 A1 * | 11/2004 | Smith | 381/67 |
| 2005/0020918 A1 * | 1/2005 | Wilk et al. | 600/439 |
| 2005/0113703 A1 * | 5/2005 | Farringdon et al. | 600/509 |
| 2005/0132290 A1 * | 6/2005 | Buchner et al. | 715/702 |
| 2005/0255434 A1 * | 11/2005 | Lok et al. | 434/262 |
| 2006/0073447 A1 * | 4/2006 | Bjork et al. | 434/218 |
| 2006/0247733 A1 * | 11/2006 | Amer | 607/48 |
| 2007/0038164 A1 * | 2/2007 | Afshar | 601/47 |
| 2007/0058818 A1 * | 3/2007 | Yoshimine | 381/67 |
| 2007/0178430 A1 * | 8/2007 | Lecat | 434/266 |
| 2007/0276278 A1 * | 11/2007 | Coyle et al. | 600/529 |
| 2008/0013747 A1 * | 1/2008 | Tran | 381/67 |
| 2008/0131855 A1 * | 6/2008 | Eggert et al. | 434/266 |
| 2008/0138778 A1 * | 6/2008 | Eggert et al. | 434/262 |
| 2008/0138779 A1 * | 6/2008 | Eggert et al. | 434/266 |
| 2008/0138780 A1 * | 6/2008 | Eggert et al. | 434/266 |
| 2009/0117526 A1 * | 5/2009 | Lecat | 434/266 |
| 2009/0117527 A1 * | 5/2009 | Lecat | 434/266 |
| 2009/0131759 A1 * | 5/2009 | Sims et al. | 600/301 |
| 2009/0256801 A1 * | 10/2009 | Helmer | 345/156 |
| 2010/0062407 A1 * | 3/2010 | Lecat | 434/262 |
| 2010/0279262 A1 * | 11/2010 | Lecat | 434/266 |
| 2013/0196302 A1 * | 8/2013 | Lecat | 434/266 |
| 2013/0252219 A1 * | 9/2013 | Lecat | 434/266 |
| 2013/0330699 A1 * | 12/2013 | Eggert et al. | 434/266 |
| 2014/0087343 A1 * | 3/2014 | Lecat | 434/266 |
| 2014/0220529 A1 * | 8/2014 | Eggert et al. | 434/266 |

OTHER PUBLICATIONS

International Search Report for PCT application No. PCT/USO5/38150 dated May 26, 2006.

Westwood, J.D., et al., The Virtual Standardized Patient, Medicine Meets Virtual Reality 2000; eds, IOS Press.

Sturman et al., "A survey of glove-based input," IEEE Computer Graphics and Applications, vol. 14, No. 1, (1994) pp. 30-39.

Bickley et al, "Bates' Guide to Physical Examination and History Taking," Eighth Edition, Lippincott Williams & Wilkins, A Wolters Kluwer Company, Table of Contents, 2003, 17 pages.

* cited by examiner

SYSTEM, METHOD AND MEDIUM FOR SIMULATING NORMAL AND ABNORMAL MEDICAL CONDITIONS

RELATED APPLICATION

This application claims the priority of U.S. Provisional Patent Application No. 60/621,084, filed on Oct. 25, 2004, which is incorporated herein by reference in its entirety.

STATEMENT AS TO RIGHTS TO INVENTIONS MADE UNDER FEDERALLY SPONSORED RESEARCH AND DEVELOPMENT

The present invention is supported in part by the Naval Health Research Center through NAVAIR Orlando TSD under contract N61339-03-C-0157. The Government may have certain rights in the invention.

FIELD OF THE INVENTION

The present invention is directed generally to simulating medical conditions and, more particularly, to transmitting an indication of the medical condition(s) to a recipient to aid in the diagnosis of various medical condition(s).

BACKGROUND OF THE INVENTION

To become clinically competent physicians, medical students must develop knowledge and skills in many areas of both the art and science of medicine. Three areas are emphasized in medical students' early clinical training: doctor-patient communication, eliciting the patient history, and performing the physical exam. Standardized patients (SPs), individuals trained to realistically portray patients, are commonly employed to teach and assess medical students in those three areas. By working with SPs, students gain the opportunity to learn and practice the skills of doctor-patient communication, such as eliciting the patient history, conducting the physical exams, and other clinical skills in a safe setting. SPs also provide a way to reliably test students' clinical skills in a realistic setting, interacting with a person. The range of clinical problems an SP can portray, however, is limited. They are typically healthy individuals with few or no abnormal physical findings. While some can be trained to simulate physical abnormalities (e.g., breathing through one lung, voluntarily increasing blood pressure, etc.), there are many abnormalities they cannot simulate.

One way to supplement what students learn from SPs is for the students to separately learn from and practice on simulators. A variety of mechanical or computer-based simulators are now used in medical education, including software for testing clinical reasoning and diagnostic skills, computer simulations of physiological processes, and physical models for practicing selected procedural skills. For example, a completely virtual SP (e.g., an interactive computer program) has been tried before by Hubal et al., as described in "The Virtual Standardized Patient," *Medicine Meets Virtual Reality* 2000 (J. D. Westwood et al., eds., IOS Press), who utilized natural language processing and virtual patients that exhibit emotion in a realistic context to provide completely automatic yet unscripted training sessions. A key limitation to these simulators is that their users (e.g., medical students) do not interact with a live person (a patient or SP). Human-computer interaction brings a different set of psychological concerns than does the human-human interaction of a doctor-patient examination. A significant level of immersion is needed to overcome the human-computer interaction aspects so that there is appreciable transfer of training with regard to patient interaction and diagnosis. This level of immersion and interactivity has not been reached and may not be achievable in a totally virtual form with today's technology. Augmenting SPs with the ability to simulate abnormal physical findings would expand the opportunities for students to learn more clinical skills in a realistic setting with a real person (SP) while practicing their doctor-patient communication skills.

In addition, there is currently a need for expanding the breadth of indications associated with known medical conditions that may be portrayed by an SP. For example, with a real or standardized patient, a student is limited to hearing only the sounds of that single person. Learning a variety of sounds has traditionally required examining many patients over time, often without direct supervision and feedback. Commercially available recordings of heart and lung sounds exist, but using them ignores the process of locating the sources of sounds (e.g., correct placement of the stethoscope) and excludes simultaneous interactions with a patient.

Augmenting SPs with the capability of portraying patients with an increased range of medical conditions would make the use of SPs an even more valuable teaching tool. The present invention is directed to these and other important ends.

SUMMARY OF THE INVENTION

The present invention provides a system, method and medium for simulating medical conditions to facilitate medical training, that utilizes a roaming device configured to be mobile; a positioning device configured to determine location information of the roaming device; and a computing device configured to receive the location information, compare the location information with a predetermined set of regions, and transmit information indicative of a medical condition when the location information coincides with the predetermined set of regions.

In at least one aspect of the invention, the location of a roaming device is determined by a positioning device and transmitted to a computing device. In some embodiments, a magnetic tracking system is used to determine the location information of the roaming device. In other embodiments, an optical tracking system is used to determine the location information of the roaming device. In other embodiments, sensor devices are used to determine the location information of the roaming device. In some embodiments, the positioning device is a sensor placed on a vest worn by the subject being examined. The computing unit calibrates the location of the roaming device according to the individual body morphology or physical movements of the subject The computing unit is connected to a computer, either as a separate unit or comprised within the computer. The computer contains software for comparing the location of the roaming device with a predetermined set of regions. When the location information of the roaming device coincides with the predetermined set of regions, information indicative of a medical condition is transmitted to an output device connected to the computer. The output device can be, for example, a stethoscope earpiece or a speaker connected to the computer, and the information indicative of a medical condition can be, for example, a sound file selected from a computer data repository. In some embodiments, the sound file can be played through the speaker in surround sound to specify the sound source location to the location of the object. A touch switch on the roaming device can control playback of the computer file, such that playback only occurs when the roaming device is touching the subject.

In accordance with the invention, information indicative of a medical condition is transmitted when the location of the roaming device coincides with a predetermined set of regions. Such regions include positions over the subject's actual heart, lungs, carotid and renal arteries, aorta, and abdomen. Examples of medical conditions that may be simulated using the invention include: bronchitis, heart failure, lung consolidation, pneumonia, atelectasis, pleural effusion, pneumothorax, chronic obstructive pulmonary disease, emphysema, asthma, healthy lung function, mitral valve prolapse, mitral regurgitation, mitral stenosis, pulmonic stenosis, aortic stenosis, aortic regurgitation, ventricular septal defect, pericarditis, healthy heart function, bowel obstruction, renal artery bruits, normal abdominal function, and carotid artery bruits.

In one aspect of the invention, the roaming device is a stethoscope and the information indicative of a medical condition is transmitted as a sound played through the earpiece of the stethoscope. The sound is either a naturally occurring sound or a digitally processed or altered sound. Examples of sounds heard through the stethoscope in accordance with the invention include normal breath sounds, crackles, wheezes, stridor, pleural rub, normal heart sounds, pathologic splitting, murmurs, clicks, gallops, pericardial friction rub, venous hum, bowel sounds, and bruits.

In yet another aspect of the invention, the roaming device is a specialized glove configured to transmit information indicative of a medical condition when the location of the glove coincides with a predetermined set of regions. When the glove detects tactile feedback at a predetermined region, a sound corresponding to a medical condition is selected by the computer for playback into the earpiece of a stethoscope or through a speaker connected to the computer.

The invention also provides a stethoscope comprising an earpiece and a headpiece, configured to transmit sound indicative of a medical condition when the location of the headpiece coincides with a predetermined set of regions. A touch switch on the headpiece of the stethoscope can be used to control the transmission of sound played through the earpiece.

DETAILED DESCRIPTION OF THE INVENTION

For the purposes of promoting an understanding of the principles of the invention, reference will now be made to specific embodiments and specific language will be used to describe the same. It will nevertheless be understood that no limitation of the scope of the invention is thereby intended, such alteration and further modifications of the invention, and such further applications of the principles of the invention as illustrated herein, being contemplated as would normally occur to one skilled in the art to which the invention relates. Also, it is to be understood that the phraseology and terminology employed herein are for the purpose of description and should not be regarded as limiting.

Figure 1:
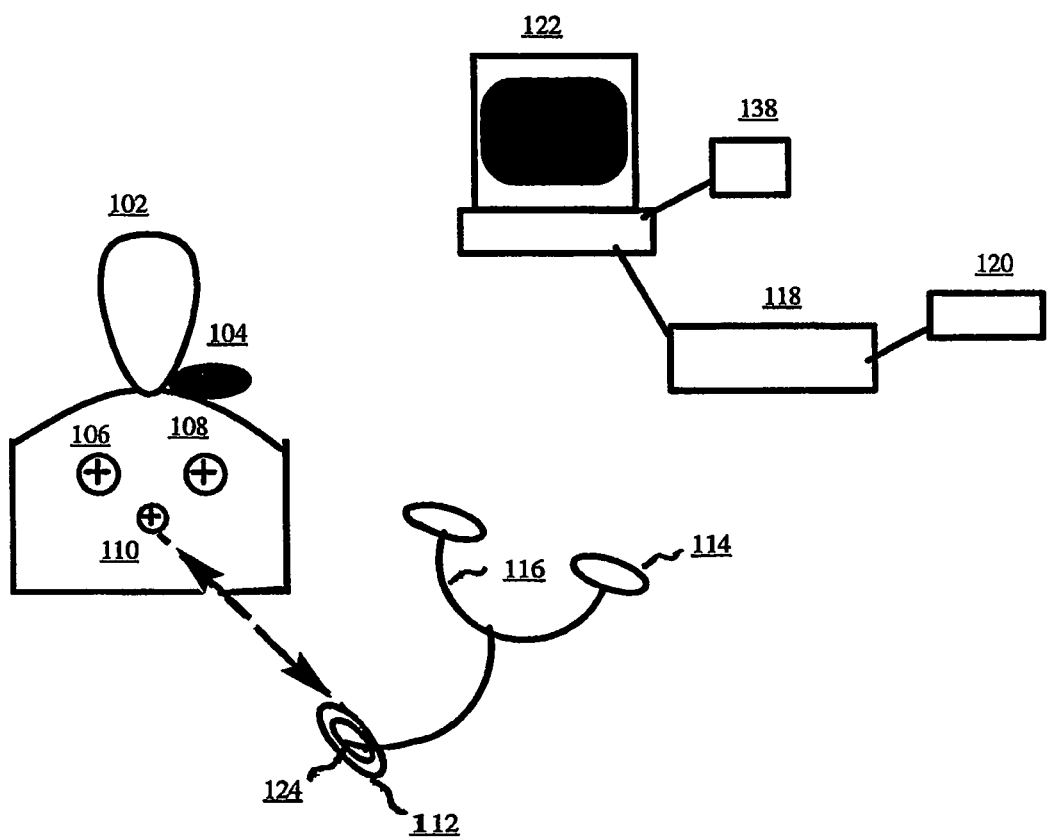
FIG. 1 is a system diagram in accordance with an exemplary embodiment of the invention.

FIG. 1, generally at 100, is a system diagram of an exemplary embodiment of the invention. Subject 102 may be, for example, an artificial person, such as a mannequin, or a living person, such as a normal patient or a standardized patient. As used herein, a standardized patient (SP) refers to an individual trained to, or who otherwise can, realistically portray a patient. A user examining subject 102 with object 116, such as a stethoscope, would not receive an indication of the subject's actual medical condition through output device 114 (e.g., actual heart beat sounds). Instead, the user receives a transmission of a computer file from computer 122 that simulates a medical condition, when roaming tracking device 112 on object 116 is located at a position or a region associated with the medical condition (e.g., position 110 in FIG. 1).

Figure 2:
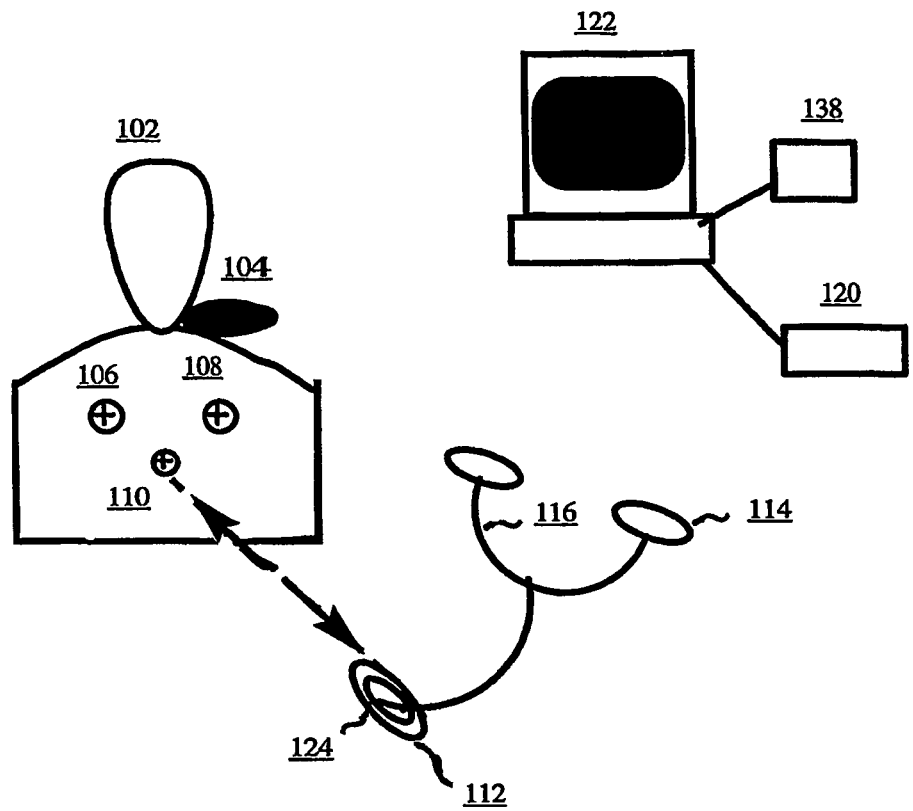
FIG. 2 is a system diagram in accordance with an exemplary embodiment of the invention.

In accordance with some embodiments of the invention, low-frequency magnetic field technology is used to determine the location of roaming tracking device 112 on object 116. Transmitting device 120, stationary tracking device 104, roaming tracking device 112, and computing unit 118 provide a system for determining the location of roaming tracking device 112 on object 116 with respect to subject 102. Transmitting device 120 can be, for example, an electromagnetic field generator, which generates electromagnetic signals that are transmitted to tracking devices, such as magnetic sensors, within a known operating radius of device 120. In FIG. 1, stationary tracking device 104 is on subject 102 and roaming tracking device 112 is on object 116, with both tracking devices within the operating radius of transmitting device 120. Both stationary tracking device 104 and roaming tracking device 112 are connected to computing unit 118. FIG. 1 shows computing unit 118 as a separate device connected to computer 2. Computing unit 118 can also be comprised in computer 122, as shown in FIG. 2. FIG. 1 also shows that both connections from stationary tracking device 104 and roaming tracking device 112 to computing unit 118 are connected via communication links. Communication links can be either with a cable, such as a serial cable, USB connection, or standard telephone wire connection, or wireless, such as Bluetooth, or any other known short distance wireless communication technology. Transmitting device 120, tracking devices 104 and 112, and computing unit 118 are available commercially as a single electromagnetic tracking system, such as the Polhemus Fastrak (Polhemus, Colchester, Vt.). Other commercially available tracking systems that may be used in the invention include the Patriot or Liberty from Polhemus and Flock of Birds, MiniBird, Nest of Birds, or PC Birds from Ascension Technology (Ascension Technology, Milton, Vt.).

The locations of tracking devices 104 and 112 in space are calculated by computing unit 118 using signals received by transmitting device 120. For example, roaming tracking device 112 transmits signals indicative of its position to computing unit 118. Software associated with computing unit 118 then computes the location of roaming tracking device 112. Computing unit 118 similarly computes the location of stationary tracking device 104. Preferably, computing unit 118 provides location information as substantially instantaneous updates of position (e.g., X, Y, and Z Cartesian coordinates) and/or orientation (e.g., azimuth, elevation, and roll). In embodiments of the invention, orientation may be measured, for example, as direction cosines, Euler angles, or quaternions.

From the location measurements obtained for tracking devices 104 and 112 with respect to transmitting device 120, computing unit 118 determines the location of tracking devices 104 and 112 with respect to each other. More specifically, the location of roaming tracking device 112 is determined with respect to the location of stationary tracking device 104 by computing unit 118. Therefore, computing unit 118 determines the location of roaming tracking device 112 relative to the reference frame of subject 102. Computing unit 118 thus provides dynamic location information that is generated according to the individual reference frames of different subjects.

In accordance with various embodiments of the invention, the correct placement of roaming tracking device 112 on subject 102 correlates with the generation of feedback indicative of a known medical condition to the user. Position and orientation measurements of roaming tracking device 112 are transmitted from computing unit 118 to computer 122, and transformed into a computer readable format utilizing any standard, commercially available software devised for making tracking data available for other applications. For example, software such as TRACKD (VRCO, Virginia Beach, Va.) may be used to transform tracking measurements of roaming tracking device 112 into a computer readable format. As shown in FIG. 1, computing unit 118 is connected to computer 122 using a cabled connection. This connection may be, for example, a serial cable, USB connection, or standard telephone wire connection. In another embodiment, computing unit 118 is connected to computer 122 using a wireless connection. This wireless connection may be, for example, a Bluetooth connection or any other known short distance wireless communication technology.

Computer 122 contains a data repository of computer files. Each file is programmed to generate an indication associated with a known medical condition. The location of roaming tracking device 112 with respect to subject 102, as computed by computing unit 118 and transformed into computer readable format, is then used by software running on computer 122 to determine which computer file, if any, is selected for playback into output device 114 connected to computer 122. The computer software compares the location of roaming tracking device 112 on object 116 to a previously recorded map of predetermined "hot zone" locations (e.g., regions) on subject 102. A computer file is selected for playback only when the location of roaming tracking device 112 on object 116 is within a predetermined operating radius of a "hot zone." For example, a computer file programmed to play a certain sound associated with a specific heart defect is selected for playback only when roaming tracking device 112 on object 116 is within the predetermined operating radius of "hot zone" 110 located over the subject's actual heart. The operating radius of a "hot zone" depends on its location and on the medical condition being simulated, and can be, for example, about 1 inch, or can be determined by one skilled in the art and adjusted for individual subjects and medical conditions to be simulated.

The computer file selected for playback is transmitted from computer 122 to output device 114. Output device 114 can be, for example, a stethoscope earpiece or a speaker. In some embodiments, a sound file can be transmitted in surround sound through the speaker to specify the sound source location to the location of object 116. FIG. 1 shows that computer 122 is connected to output device 114 using a cabled connection. This connection may be, for example, a serial cable, USB connection, or standard telephone wire connection. In another embodiment, computer 122 is connected to output device 114 using a wireless connection. This wireless connection may be, for example, a Bluetooth connection or any other known short distance wireless communication technology.

As used herein, a "hot zone" refers to a location on the body of subject 102 that triggers the playback of a corresponding computer file. "Hot zone" locations on a subject correspond with one or more simulated medical conditions. For example, if a particular cardiovascular condition is desired to be simulated, one or more "hot zones" corresponding to the particular heart condition will be located, for example, over the subject's anterior chest and/or major arteries, such as the carotid or renal artery. As another example, if a particular lung condition is desired to be simulated, one or more "hot zones" corresponding to the particular lung condition will be located, for example, over the subject's lungs. Other "hot zones" in accordance with the invention include areas generally examined by physicians during the pulmonary examination, such as the 26 areas described in *Bates' Guide to Physical Examination and History Taking* (Bickley & Szilagyi, Philadelphia: Lippincott William & Wilkons 2003), incorporated by reference in its entirety.

One skilled in the art may also appreciate that the location in space of a given "hot zone" will vary among subjects. For example, "hot zone" locations may vary depending on the individual subject's body morphology type (for example, obese v. thin body types or male v. female body types), or if a subject shrugs her shoulders or twists. In one or more embodiments of the invention, tracking device measurements are recalibrated to account for these variations and deviations among different subjects. Position measurements for stationary tracking device 104 on subject 102 with respect to transmitting device 120 are compared by computing unit 118 to position measurements obtained using a frame of reference as measured, for example, by an tracking device attached to a subject of average height, weight, and build. Any deviations in the position measurements for stationary tracking device 104 from the neutral position are accordingly subtracted from the position measurements obtained for roaming tracking device 112 on object 116. In some embodiments, neoprene vests of standard sizes (for example, XS to XXL) labeled with "hot zone" locations and calibration reference points can be used for calibrating the system according to any individual subject's morphological type. The subject can wear a vest of appropriate size for a short period of calibration to individualize the "hot zone" pattern for the subject.

When the location of roaming tracking device 112 on object 116 is within the range of a "hot zone," a computer file is selected for playback and transmitted from computer 122 to output device 114. In some embodiments, roaming tracking device may include a touch switch 124. In operation, touch switch 124 enables output device 114. In other words, a user is not able to detect through output device 114 the playback of the selected computer file unless touch switch 124 is in the "closed" position. Computer 122 transmits the playback of a selected file to touch switch 124, which is connected to output device 114. If touch switch 124 is in the "open position," the playback transmission to output device 114 is blocked. However, touch switch 124 closes upon contact with subject 102 into the "closed" position, allowing the playback transmission to be detected through output device 114 by the user. Touch switch 124 can be a standard, commercially available SDPT switch with ¾" roller lever, such as Radio Shack catalog #275-017, modified by removing the roller from the switch.

Figure 5:
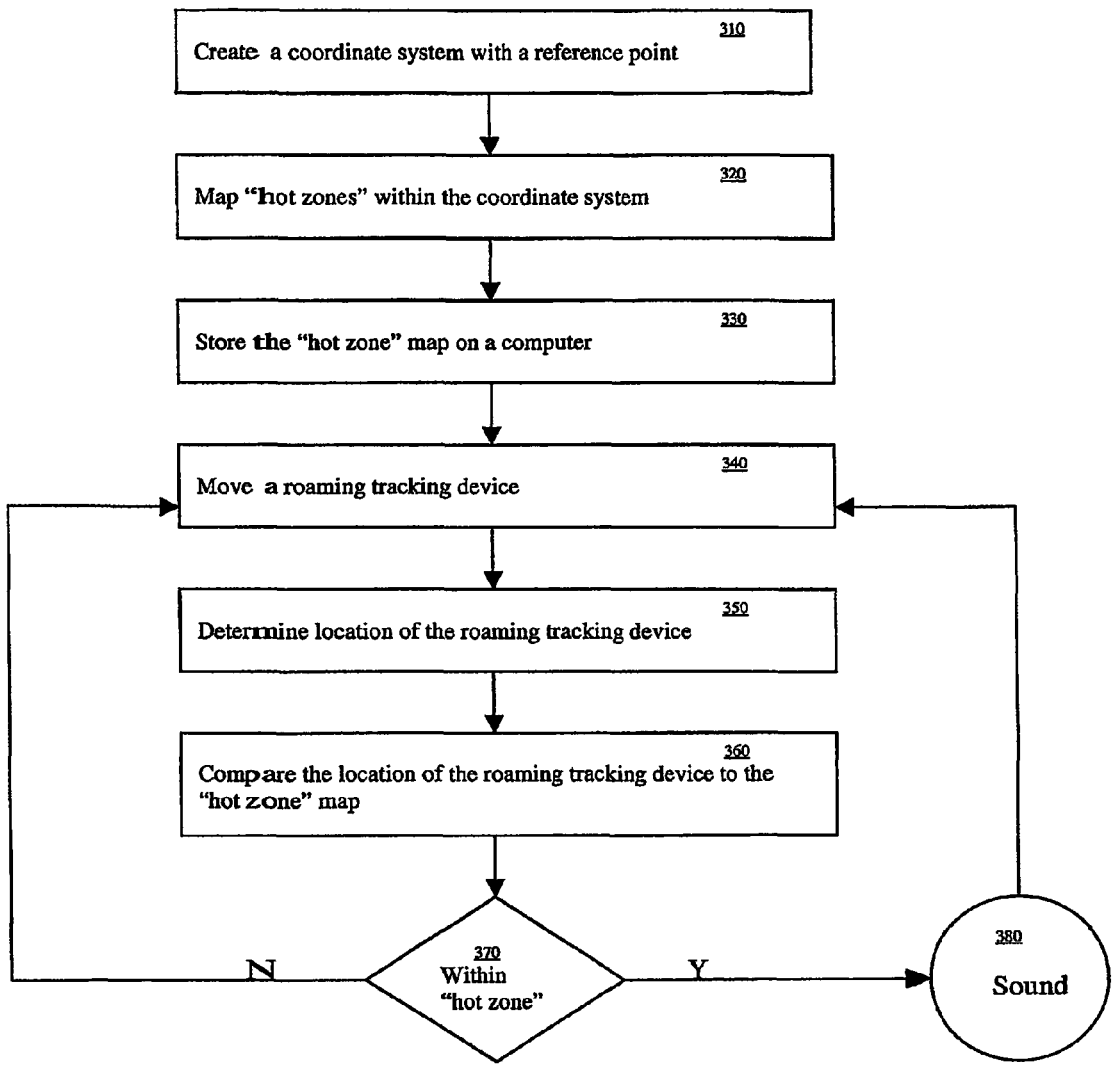
FIG. 5 is a flow diagram illustrating a method in accordance with an exemplary embodiment of the invention.

FIG. 5 is a flow diagram illustrating the steps performed according to an exemplary embodiment of the invention. At step 310, a coordinate system with a reference point is created with a computing device. The reference point can be, for example, a stationary tracking device attached to the subject. At the next step, step 320, "hot zone" locations are mapped within the coordinate system, using information known to one of skill as described above. At step 330, the "hot zone" map is stored on the computing device. A roaming tracking device is then moved over the subject at step 340. The computing device determines the location of the roaming tracking device at step 350, then compares the location of the roaming tracking device to the pre-recorded "hot zone" map at step 360. If the location of the roaming tracking device is within the range of a "hot zone" at step 370, the computing device triggers the playback of sound through an output device, such as a stethoscope earpiece or a speaker connected to the computing device, at step 380. The sound is played continuously as long as the roaming tracking device is within the range of the "hot zone" location.

Figure 3:
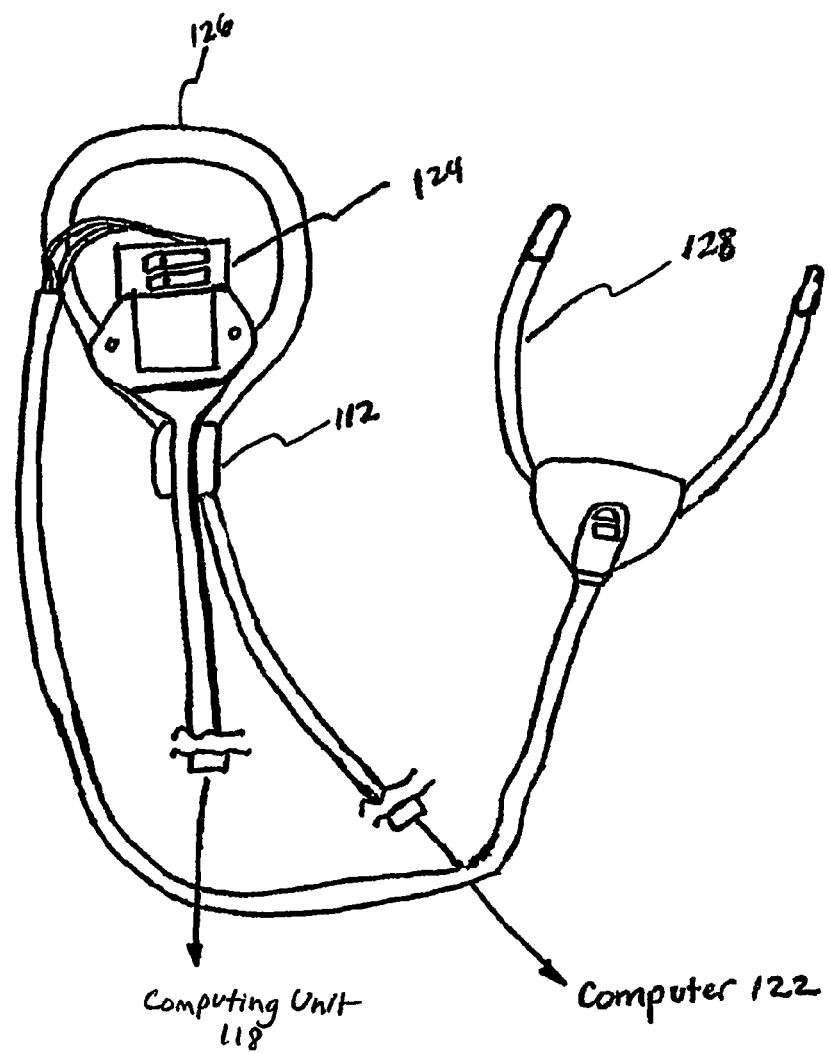
FIG. 3 illustrates a stethoscope in accordance with an exemplary embodiment of the invention.

In one or more embodiments of the invention, object 116 is a standard electronic stethoscope, such as, generally the Androscope i-stethos model IS-28A00 (Andromed, Inc., St. Laurent, Quebec), modified as described herein. FIG. 3 shows an exemplary stethoscope in accordance with the invention. As shown in FIG. 3, touch switch 124 and roaming tracking device 112 are mounted on headpiece 126 of object 116. Earpiece 128 (corresponding to output device 114 in FIG. 1) is a separate device from headpiece 126. In some embodiments of the invention, headpiece 126 and earpiece 128 are incorporated in a single device. Earpiece 128 is connected to the audio output device of computer 122.

Transmission of a computer sound file from computer 122 to earpiece 128 correlates with correct placement of headpiece 126 on subject 102. In one or more embodiments of the invention, the sound file is a .wav file. However, other sound files, such as .mp3 files, may be used. The sound file may correspond to either a naturally occurring sound (e.g., a normal heartbeat) or to a sound that has been digitally processed (e.g., modifying a normal heartbeat to sound like an abnormal heartbeat) or digitally altered (e.g., adding extra sounds to normal heart sounds to simulate a valvular defect, or adding wheezes to breath sounds to simulate asthma). Commercially available software for digital signal processing may be used in connection with embodiments of the invention. For example, WaveWarp from SoundsLogical (Glasgow, Scotland UK) may be used.

Computer playback of the sound file is timed to correspond to the actual inspiration and expiration of the subject. A sound sensing/modifying approach is used where the computer receives input device information on the subject's inspiration/expiration and adjusts the timing of the lung sounds accordingly. Information on the subject's breathing pattern is obtained using a subject-controlled actuator switch or a plethysmograph to monitor chest movement.

Figure 4:
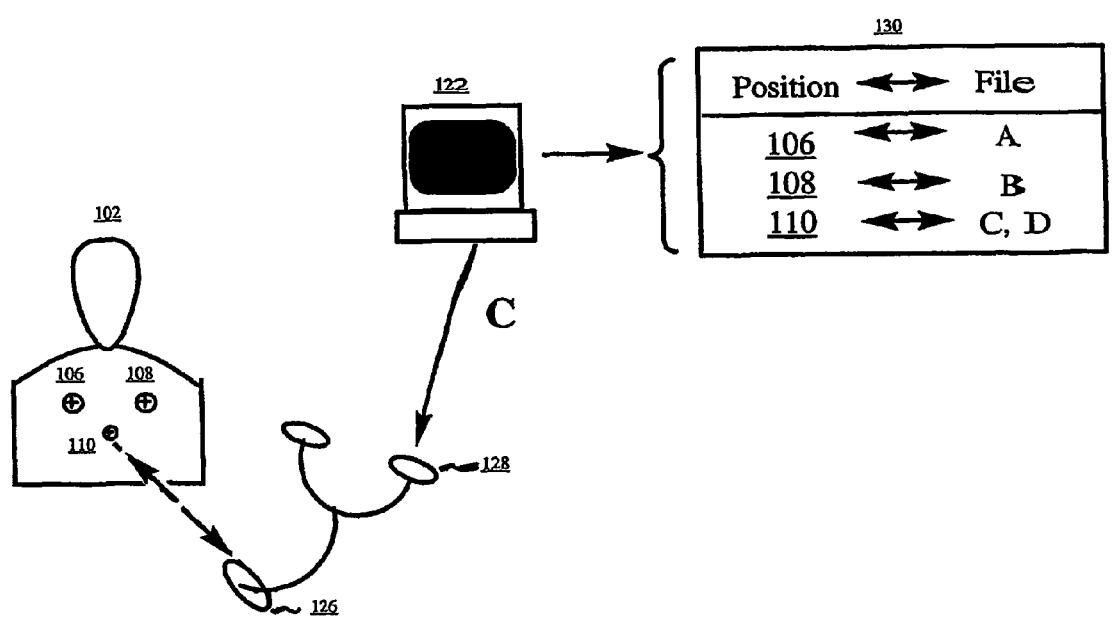
FIG. 4 is a diagram in accordance with an exemplary embodiment of the invention.

FIG. 4 is a diagram of an exemplary embodiment of the invention. A sound file transmitted to earpiece 128 provides auscultatory feedback to the user when the user places headpiece 126 on an appropriate "hot zone." For example, when headpiece 126 is located on "hot zone" position 110 over the location of the subject's actual heart, computer 122 may select sound file C corresponding to "hot zone" 110, generating abnormal sounds associated with, for example, a heart defect, for playback into earpiece 128. Alternatively, when headpiece 126 is located on "hot zone" position 110, computer 122 may select sound file D also corresponding to "hot zone" 110, generating normal sounds associated with a normal heart. As chart 130 illustrates, computer 122 will select sound file A when headpiece 126 is located on "hot zone" position 106, and the computer will select sound file B when headpiece 126 is located on "hot zone" position 108. The sound files selected for playback into the stethoscope correspond to sounds commonly auscultated during the physical examination of a patient. The auscultation of sounds associated with either a normal or an abnormal medical condition is used, for example, by a user to make a medical diagnosis regarding the medical condition of the subject. As used herein, "auscultation" refers to the act of listening for sounds made by internal organs, such as the heart, lungs, abdomen, and major arteries, to aid in the medical diagnosis of a subject.

In accordance with the invention, the auscultated sound corresponds to the particular medical condition that is simulated by the subject. In one embodiment, a heart condition is simulated by the playback of heart-associated sounds. Examples of heart-associated sounds that may be generated, and the associated heart condition that is simulated, include: normal heart sounds, pathologic splitting, murmurs, clicks, gallops, pericardial friction rub, venous hum, and carotid artery bruits, for simulating healthy heart function, heart failure, mitral valve prolapse, mitral regurgitation, mitral stenosis, pulmonic stenosis, aortic stenosis, aortic regurgitation, ventricular septal defect, and pericarditis. In another embodiment, a lung condition is simulated by the generation of lung-associated sounds. Examples of lung-associated sounds that may be generated, and the associated lung condition that is simulated, include: normal breath sounds, crackles, wheezes, stridor, and pleural rub, for simulating healthy lung function, bronchitis, lung consolidation, pneumonia, atelectasis, pleural effusion, pneumothorax, chronic obstructive pulmonary disease, emphysema, and asthma. In another embodiment, an abdominal condition is simulated by the generation of abdominal-associated sounds. Examples of auscultation sounds that may be generated, and the associated abdominal condition that is simulated, include: bowel sounds and bruits, for simulating bowel obstruction, renal or aortic artery bruits, and normal abdominal function.

In another embodiment of the invention, an optical tracking system that utilizes optical motion capture may be used for determining the location of a roaming device. Optical motion capture is the tracking of markers, such as LED markers, on an object over time. Generally, cameras are placed on the perimeter of a capture area to track markers placed on the object. Using an optical tracking system, active marker positions are detected by camera sensors and transmitted to a central processor, which calculates and stores the coordinate positions for the markers. Optical tracking systems such as ARToolkit (Human Interface Technology Laboratory, University of Washington, Seattle, Wash.), PhaseSpace optical motion capture systems (PhaseSpace, San Leandro, Calif.), HiBall-3000 (3rdTech, Inc. Chapel Hill, N.C.), Vicon small camera systems (Vicon Motion Systems, Inc., Lake Forest, Calif.), the Hawk System (Motion Analysis Corp., Santa Rosa, Calif.), and the Eagle System (Motion Analysis) may be used in conjunction with the invention.

Figure 6:
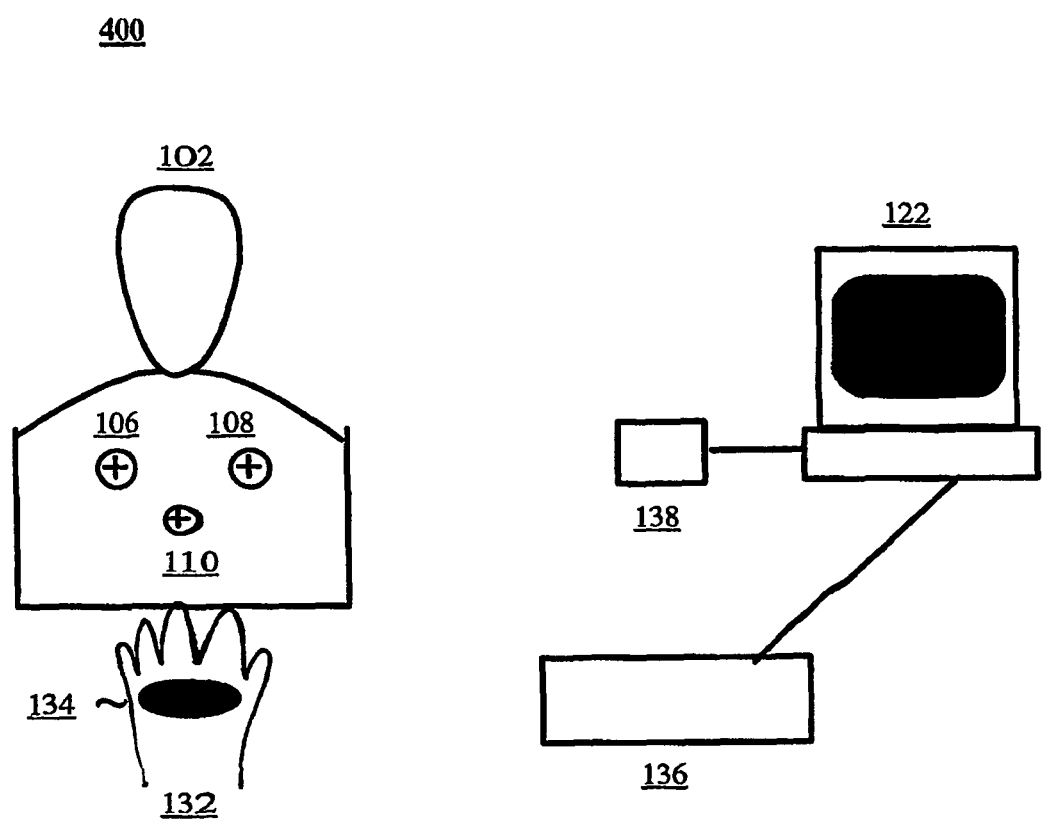
FIG. 6 is a system diagram in accordance with an exemplary embodiment of the invention.

FIG. 6, generally at 400, is a system diagram of an exemplary embodiment of the invention. An optical marker 134 is placed on the user's hand 132 or on an object held in the user's hand, such as a stethoscope headpiece, while the user performs an examination of the subject 102. A camera sensor 136, placed within a known operating radius of optical marker 134 and connected to computer 122, detects the position in three dimensions of the optical marker 134. Various software associated with computer 122 then determines the location of optical marker 134 relative to the location of camera sensor 136, converts the position measurements to a computer readable format, and compares the location of optical marker 134 to a previously recorded map of predetermined "hot zone" locations on subject 102. When the user taps the back of the subject on a "hot zone" location, for example "hot zone" location 110, a computer file corresponding to the "hot zone" is transmitted from the computer 122 for playback to an output device 138, such as a speaker connected to the computer or a stethoscope earpiece. In some embodiments, the computer file is transmitted for playback to a speaker using surround sound software to specify the sound source location to the location of the user's hand 132. Commercially available software for surround sound broadcasting may be used in connection with embodiments of the invention. For example, Maven3D from Emersys (Daejeon, South Korea) may be used.

Figure 7:
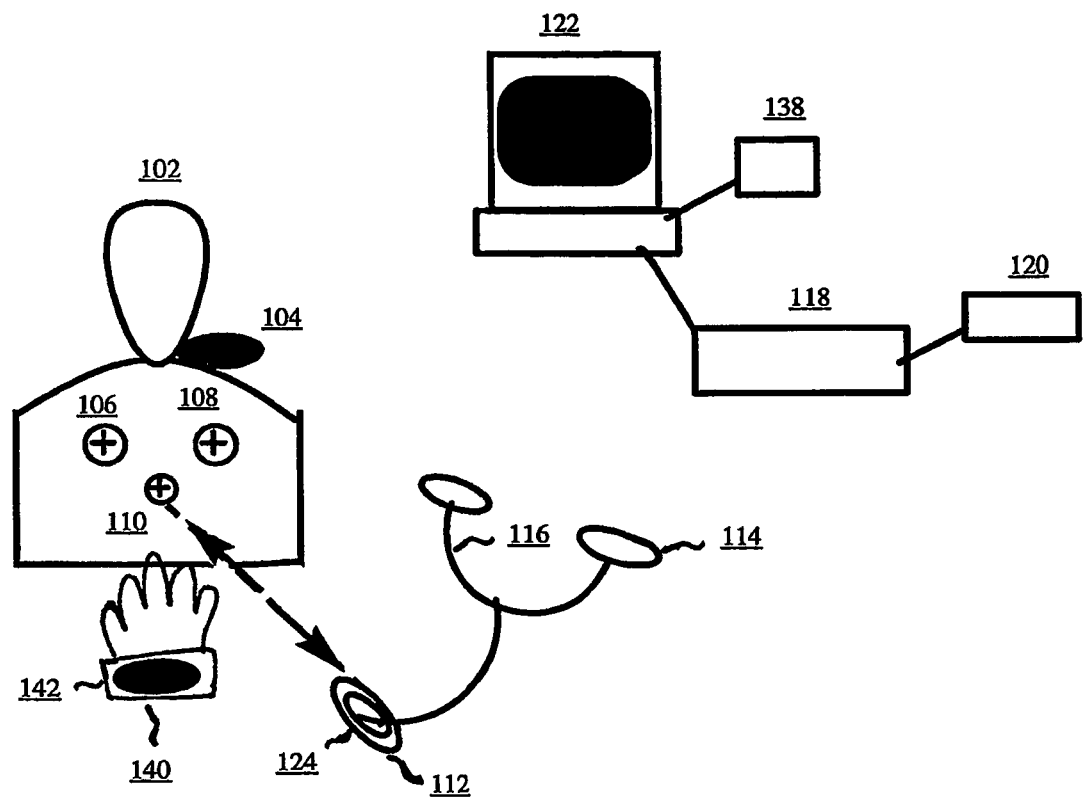
FIG. 7 is a system diagram in accordance with an exemplary embodiment of the invention.

In another embodiment of the invention, a specialized glove 140, such as, generally the CyberTouch or the CyberGlove (Immersion Corp., San Jose, Calif.) is used, at least in part, to simulate a medical condition. FIG. 7, generally at 500, is a system diagram showing an exemplary embodiment of the invention. Glove 140 is mounted at the wrist portion with roaming tracking device 142, which transmits signals indicative of its position to computing unit 118. Measurements of the position of roaming tracking device 142 thus provides the general location of glove 140 from the wrist position and a plurality of fiberoptic sensors can be embedded in glove 140 to measure the flexion of the fingers. Glove 140 is also connected to computer 122 and is capable of transmitting various information to the computer. For example, when the user taps the back of subject 102 on a "hot zone" location, glove 140 detects the vibrations emanating from the body of subject 102 and transmits a signal to computer 122. The signal triggers the playback of a computer file corresponding to the "hot zone," transmitted from computer 122 for playback into output device 114 or through speaker 138 connected to computer 122. The computer file can be, for example, a sound file transmitted in surround sound through speaker 138. In a more specific example, the user may tap the back of subject 102 on "hot zone" position 110 over the subject's lungs. Computer 122 would correlate the position of glove 140, as determined by computing unit 118, with a sound file that generates echoic or dull lung sounds, for playback into output device 114 or through speaker 138. Various other sound files can be accessed to simulate different medical conditions.

In another embodiment of the invention, a sensor system is used to determine the location of a roaming device. For example, sensing devices configured to detect when a marker moves within an operating radius can be fastened or mounted to "hot zone" locations on a vest worn by the subject. When a marker, mounted on a user's hand or on an object such as a stethoscope in the user's hand, is moved within a "hot zone," the sensing device communicates this information to a computer, and software associated with the computer triggers the playback of a sound file through an output device such as a computer speaker or the earpiece of the stethoscope. In some embodiments, the sensing device can be used as the roaming device to detect markers fastened to the "hot zone" locations on the vest. Sensing devices configured to detect markers are known and readily available to one skilled in the art.

According to one or more embodiments of the invention, the components of the system for simulating normal or abnormal medical conditions can be connected in different ways. For example, the connections can be wired, wireless, optical, electromagnetic, and the like. In addition, one or more cameras can be used to provide information and/or position data for the tracking devices. Alternatively, or additionally, tracking devices or magnetic sensors known in the art can be incorporated into the tracking system to assist in, or detect, the location of the tracking device. The functions of one or more devices can also be combined into a single device. For example, the computer can be programmed, and include appropriate hardware, to perform the functions of the tracking system. Various components can also be connected across one or more networks so that data can be exchanged and/or analyzed by others. For example, in a classroom setting, an instructor can demonstrate the appropriate locations to position the stethoscope. Appropriate signals can be sent to the computer and transmitted across a wireless network. Users in the classroom would then receive the appropriate sounds in their own stethoscopes. All such embodiments, modifications, and variations fall within the scope of the present invention.

While the invention has been illustrated and described in detail in the drawings and foregoing description, the same is to be considered as illustrative and not restrictive in character, it being understood that only the preferred embodiments have been shown and described and that all changes and modifications that come within the spirit of the invention are desired to be protected. In addition, all references cited herein are indicative of the level of skill in the art and are hereby incorporated by reference in their entirety.

We claim:

1. A system for simulating medical conditions to facilitate medical training, the system comprising:
    markers to be positioned at locations on a subject's body, the markers respectively having detection zones corresponding to a predetermined set of regions;
    a sensing device to detect the markers; and
    an earpiece to be worn by a user, the earpiece coupled to the sensing device to provide sounds when the markers are detected, the sounds being representations of sounds produced by body parts in the predetermined set of regions.

2. The system of claim 1, wherein the sounds are naturally occurring sounds.

3. The system of claim 1, wherein the sounds are digitally processed sounds.

4. The system of claim 1, wherein the sounds are altered sounds.

5. The system of claim 1, wherein the sounds include at least one of:
    normal breath sounds, crackles, wheezes, stridor, pleural rub, normal heart sounds, pathologic splitting, murmurs, clicks, gallops, pericardial friction rub, venous hum, bowel sounds, and bruits.

6. The system of claim 1, wherein the sounds represent a medical condition, the medical condition is at least one of: bronchitis, heart failure, lung consolidation, pneumonia, atelectasis, pleural effusion, pneumothorax, chronic obstructive pulmonary disease, emphysema, asthma, healthy lung function, mitral valve prolapse, mitral regurgitation, mitral stenosis, pulmonic stenosis, aortic stenosis, aortic regurgitation, ventricular septal defect, pericarditis, healthy heart function, bowel obstruction, renal or aortic artery bruits, normal abdominal function, and carotid artery bruits.

7. The system of claim 1, wherein the predetermined set of regions comprises regions over the heart, lungs, carotid artery, renal artery, and abdomen of a subject being examined.

8. The system of claim 1, wherein the sensing device is part of a training stethoscope configuration that communicates with a computer.

9. The system of claim 1, wherein the earpiece is a stethoscope earpiece.

10. The system of claim 1, wherein the markers are placed on a vest worn by the subject.

11. The system of claim 1, wherein the sensing device and the markers are in short distance wireless communication.

12. The system of claim 8, wherein the training stethoscope configuration receives signals indicative of the sounds through wireless communication with the computer.

13. The system of claim 12, wherein the computer contains a data repository of computer files, and wherein the files are programmed to generate an indication associated with a known medical condition.

14. The system of claim 1, wherein the sensing device communicates with a computing component that assists with providing the sounds.

15. The system of claim 1, wherein the subject is a human subject.

* * * * *